United States Patent [19]
Adelman

[11] 3,945,371
[45] Mar. 23, 1976

[54] APPARATUS FOR INSPECTION AND SAMPLING IN RESTRICTED APERTURE CAVITIES EMPLOYING FIBRE OPTICS

[76] Inventor: Stuart Lee Adelman, 40 Gough Way, Cambridge CB3 9LN, Cambridgeshire, England

[22] Filed: May 25, 1973

[21] Appl. No.: 364,531

[30] Foreign Application Priority Data

| | | |
|---|---|---|
| May 26, 1972 | United Kingdom | 25034/72 |
| Nov. 30, 1972 | United Kingdom | 55386/72 |
| Dec. 12, 1972 | United Kingdom | 57281/73 |
| Feb. 1, 1973 | United Kingdom | 5111/73 |
| May 9, 1973 | United Kingdom | 22049/73 |

[52] U.S. Cl. ............... 128/2 B; 128/2 W; 128/6; 350/96 B
[51] Int. Cl.² ............... A61B 1/00; A61B 10/00
[58] Field of Search ............... 128/2 B, 2 W, 6–9, 128/11; 350/96 B

[56] References Cited
UNITED STATES PATENTS

| | | | |
|---|---|---|---|
| 2,975,785 | 3/1961 | Sheldon | 128/6 |
| 3,021,834 | 2/1962 | Sheldon | 128/6 |
| 3,091,235 | 5/1963 | Richards | 128/6 |
| 3,132,646 | 5/1964 | Hett | 128/6 |
| 3,426,749 | 2/1969 | Jephcott | 128/11 |
| 3,643,653 | 2/1972 | Takahashi et al. | 128/6 |
| 3,815,986 | 6/1974 | Darbee | 350/96 B |
| 3,819,267 | 6/1974 | Kawahara | 128/6 X |

FOREIGN PATENTS OR APPLICATIONS

| | | | |
|---|---|---|---|
| 1,217,300 | 12/1970 | United Kingdom | 128/6 |

*Primary Examiner*—Kyle L. Howell
*Attorney, Agent, or Firm*—Julian Caplan

[57] ABSTRACT

Hand held apparatus for carrying out cervical inspections is disclosed the apparatus has a fibre optic probe and a low power light source located in the handle of the device. The image is projected to a translucent display screen used at the rear of the apparatus. The probe is provided with a removable general view unit for attaching to the end of the probe. The device also has a disposable sheath through which a sample collecting device can be inserted. The general view optical unit is arranged to have both a good depth of focus and a wide angle of vision at low illuminations.

12 Claims, 15 Drawing Figures

APPARATUS FOR INSPECTION AND SAMPLING IN RESTRICTED APERTURE CAVITIES EMPLOYING FIBRE OPTICS

The present invention relates to apparatus for examining the interior of cavities to which access can only be obtained via restricted orifices or passages.

Examples of such cavities include the internal organs of animals such as the mouth, throat, lungs, oesophagus and stomach and also the rectum and lower bowel and the vagina and cervix. However although the invention has been developed with particular reference to the problems encountered in such medical uses it also has industrial and scientific uses for example to check the interior of a structure enclosed within a sealed envelope and in checking the correct assembly of industrial devices and apparatus at remote locations.

It is thus an object of the invention to provide robust, simple, easily used optical inspection apparatus having particular advantages associated with its use in the medical diagnostic field.

Thus according to the present invention apparatus adapted to be held in the hand for inspecting a cavity, e.g. the vaginal cavity, comprises a probe for insertion into the cavity, the probe comprising optical illuminating means suitable for feeding light into the cavity, optical means suitable for collecting an image of that portion of the cavity which is illuminated and feeding the optical image to the outside of the cavity and projecting the said image onto image display means located to the rear of the probe.

The image display means may be a ground glass screen or any other suitable translucent material. Preferably the means for feeding the light into the cavity and the means for feeding the optical image out of the cavity have a total cross sectional area of less than 3.25 sq. cms.

The invention in a preferred form has further advantages in the medical diagnostic field.

In this preferred form a disposable readily releaseable sheath is used, e.g. in conjunction with disposable sample collecting devices e.g. of plastics materials. This enables the instrument to be used to carry out rapidly large numbers of inspections and sample collections, and the samples can be housed in the sheaths for subsequent examination, e.g., by specialized personnel or by automatic equipment.

Thus in this preferred form of the invention a disposable sheath is provided which encloses the said optical means and defines a longitudinal duct whereby sample collecting means can be introduced into the cavity, the sheath at least at its distal end being of transparent material.

The sheath is preferably made of rigid transparent plastics material and has a cross sectional area of not more than 3.25 sq. cms.

In one specific form the apparatus comprises a body portion carrying the probe, the said body portion housing the image display means and optical means, e.g. comprising a lens system, (i.e., a plurality of lenses) for projecting the image onto the display means (by means herein sometimes referred to as "projection system"), the body portion having a handle housing a preferably controllable light source and having means for feeding the light from the light source to the optical illuminating means in the probe, the body portion also having a passageway in which a sheath suitable for sheathing the said probe can be releaseably secured.

The probe preferably comprises fibre optic means affording the illuminating means and fibre optic means affording at least the image feeding means.

In an alternative arrangement the image display means may comprise a fibre optic cone.

There is also a need in the uses mentioned above for a simple robust apparatus which will enable both an overall inspection of a relatively large area (by means herein sometimes referred to as a "general view unit") and a more detailed inspection of a restricted area (by means herein sometimes referred to as a "close-up-unit") to be readily carried out.

Thus according to one aspect of the present invention apparatus adapted to the inspection of the interior of a cavity to which access can only be obtained via a restricted opening comprises first optical means suitable for feeding light into the cavity to illuminate at least a portion of the interior of the cavity and second optical means suitable for collecting an image of at least a portion of that part of the cavity which is illuminated and feeding the optical image to the outside of the cavity to image display means, the second optical means afford a close up unit, adapted to give a close up view of a portion of that part of the cavity which is illuminated, and the apparatus also affording at least one further unit, the general view unit, which is used in conjunction with the close up unit, to give a general view of a portion of that part of the cavity which is illuminated.

The first optical means which provide the illumination to the cavity is preferably a fibre optic bundle which may be a separate circular bundle running parallel and next to the second optical means.

However the arrangement can be made more compact if the first optical means are arranged as an annulus or sheath of fibre optic material surrounding the second optical means.

The close up unit of the second optical means is preferably an imaging fibre optic bundle located within an annular fibre optic illuminating bundle which comprises the first optical means. The close up unit supplies an optical image from the distal end of the device to the image display means.

The close up unit, e.g., the imaging fibre optic bundle comprise individual fibers which preferably have a relatively high numerical aperture e.g. at least 0.2 e.g. in the range 0.3 to 0.8 or 0.4 to 0.6 which will give the bundle a short depth of focus, e.g., 1 to 3 mm., at low illumination. Preferably the acceptance angle of each fibre element of the bundle is at least 10° e.g. 20° to 50° or 30° to 40°.

Thus at a maximum distance from the object of 3mms each fibre element observes an area 1.3 mms in diameter using a fibre of numerical aperture 0.56.

To afford easy access to cavities via a restricted opening the close up unit has a maximum outer diameter less than the inner diameter of the restricted opening e.g. for vaginal inspection less than 3.25 cms e.g. 0.2 to 2.5 cms e.g. 0.5 to 1.5 cms e.g. 1 cm.

The general view unit of the second optical means may be an optical unit adapted to be removably secured to the distal end of the probe (the end which is inserted in the cavity) e.g. it may be a lens system together with a fibre optic bundle.

The device is most conveniently used first to obtain a general view and is then adjusted to enable a close up view to be obtained. However the exact mode of use is at the discretion of the operator.

In a further alternative both general view and close up units are permanently secured in the device and an optical or mechanical switching device is provided at the rearward end of the fibre optic bundles so as to bring the image from one or other bundle only as desired to the image display means.

In the arrangement in which the first optical means is arranged as an annular sheath surrounding the second optical means, the first optical means preferably being of fibre optic material and the second optical means also preferably being of fibre optic material, the core may comprise one or more imaging units which may or may not incorporate objective lens systems or have different optical characteristics e.g. one conduit may have low numerical aperture and the other a high numerical aperture as described above. Alternatively one may incorporate an objective lens system making it a general view unit and the other without such a lens system may be a close up unit, as described above which functions primarily in proximal scan. The imaging core incorporating one or more imaging units may be enclosed by a thin metal sheath and another sheath concentric with the core but whose diameter is greater than the outer diameter of the metal sheath may be placed around the sheathed core and filled with non imaging fibre optic material as described above.

The optical illuminating means are supplied with light desirably from a self contained battery and lamp pack which is preferably rechargeable, and is incorporated in the apparatus so that it is self contained and portable and ideally can be held in one hand without fatigue to the operator.

Hitherto it had not been thought that a battery and lamp pack sufficiently compact to achieve these requirements would provide sufficient illumination. However I have appreciated that it is highly desirable to use relatively low illumination for this purpose. Thus the end face of a fibre optic bundle is made up of a number of regular shaped elements often hexagonal in cross section and at low throughput of light these are visible; contrary to what might be thought I have observed that this is an advantage when inspecting the interior of a cavity since it provides a built in raster or reference pattern for the observer and rather than interfering with observation it enables more accurate observation to be carried out.

Thus according to this aspect of the invention a means for inspecting the interior of a cavity to which access can only be obtained via a restricted opening comprises feeding light into the cavity collecting an image of at least part of that portion of the cavity which is illuminated and feeding the optical image down a fibre optic bundle made up of a regular array of fibre optic elements to the outside of the cavity to image display means, the amount of light fed into the cavity being such that the interfaces between the fibre optic elements are visible on the image display means whereby they provide a reference pattern for the observer.

This apparatus very much facilitates discussion of phenomena between observers since a gross feature can be taken as a reference point and the grid pattern be used to identify smaller features by stipulating the distances and direction from the gross feature of the smaller feature in a manner similar to the use of a map reference.

Low through put of light is similarly advantageous because extremely high levels of illumination tend to wash out the observers ability to recognise distinguishing features by minimizing contrast and color contrast and by tending to increase cross talk between individual fibres thus decreasing the signal to noise ratio of the image elements and lowering perceptual resolution i.e. the ability to perceive discrimination between features which are optically resolved.

Thus the image collecting and feeding means preferably comprise one or more fibre optic bundles made up of a regular array of fibre optic elements and the light source and optical illuminating means being such that the light output from the end of the optical illuminating means, e.g. the annulus of fibre optic material, is in the range 500 to 5000 foot Lamberts e.g. 1000 to 3000 or 1500 to 2000. This value is as measured by a photometer sold under the trade name SPECTRA BRIGHTNESS SPOTMETER produced by Photo Research Corporation of Burbank California Model TSS-SB distributed in the United Kingdom by Barnes Instrument Co. London.

The light source preferably comprises a lamp of between 1 and 30 volts and 0.05 to 2.5 amps. The power range is preferably from 0.1 to 30 watts e.g. 2 to 6 or preferably 4 watts. The filament length is preferably less than 8 mms e.g. 3 to 8 mms. The filament is preferably tungsten or a quartz-halogen system could be used.

The light is preferably led from the lamp to the first optical means, which are preferably a fibre optic bundle or annulus as described above, and fed thereinto e.g. by transillumination by a flexible fibre optic bundle e.g. that sold under the trade mark FIBROX by the Rank Organisation. I have found that light losses can be significantly reduced by certain arrangements of the lamp and the end of the flexible fibre optic bundle. I have found that the major portion of the losses are due to geometric losses. These can be minimized by placing an ellipsoidal reflector behind the lamp and placing the filament at one focus and the end of the fibre optic bundle at the other focus. Similarly a cardioidal reflector might be used. However I have found that a simpler method avoiding the need for reflectors can also be used.

In this arrangement a lamp having an envelope of constant cross section e.g. cylindrical cross section is located in a close fitting housing of cooperating cross section so that the lamp is held in substantially fixed axial position by the housing and the end of the flexible fibre optic bundle is located in a close fitting duct in the housing so that the end of the bundle is held close to the surface of the envelope of the lamp, thus closely aligning the filament of the lamp with the end of the fibre optic bundle. The spacing of the nearest part of the filament of the lamp from the end of the bundle is preferably not greater than the diameter of the bundle e.g. the bundle may have an active diameter (the internal diameter of the metal sheath) of 5.3 mms and the spacing may be from 1 to 5 mms. Also the frontal length of the filament projected onto a plane parallel to the end face of the fibre optic bundle, i.e. considered as a line source, is preferably at least 70% e.g. at least 100% or 70% to 150% of the active diameter of the bundle e.g. it may be from 4 to 7 mms with a bundle having an active diameter of 5.3 mms.

The housing for the lamp and bundle end may be of suitable plastics or metal and is designed so as to ensure that the temperature of the end of the fibre bundle does not exceed 500°C. The lamp and cable can be held in place by grub screws.

Clearly the separation between the filament and the envelope of the bulb must be sufficient to give an adequate bulb life. The front or top of the bulb is preferably flat and is placed in contact with the end of the fibre optic bundle.

The filament of the bulb preferably has a flat upper length which lies substantially parallel to the end face of the bundle and preferably extends across at least 50% of the diameter of the end face of the bundle.

Preferably the lamp and the end of the fibre optic bundle are so positioned in the housing as to locate the longitudinal axis of the fibre optic bundle along or closely adjacent to and substantially parallel to the longitudinal axis of the light source.

The lamp and fibre bundle may be located in ducts or recesses in a heat conducting block. The recesses or ducts are preferably both close fits to the surface of the envelope of the bulb and the fibre bundle. The end of the envelope of the bulb is preferably in contact with the end of the fibre optic bundle.

It has been mentioned above that the apparatus is preferably powered by a rechargeable battery and for the low illumination aspect this will most conveniently be a low power battery (to avoid the need for a transformer) and thus in order to maximize battery life it will be desirable to keep it as near full charge as possible and to recharge it as slowly as possible, i.e. so as to be compatible with the safe continuous charging rate of the battery.

This means that it is desirable to have the batteries on charge for as much of the time that the apparatus is not in use as is possible.

To this end the device is provided with an asymmetric housing e.g. it may have a handle which houses the battery or batteries and affords charging terminals, the probe affords the asymmetry with respect to the handle. An additional aspect of asymmetry may also be provided by disposing the handle out to one side of the housing.

The apparatus thus preferably has an asymmetric shape and is then provided with a carrying case having a mount providing a recess shaped to receive the apparatus in only a single orientation and affording charging terminals arranged to contact charging terminals carried by the apparatus in the correct sense when the apparatus is inserted in the recess, the carrying case having a built-in charging circuit connecting the charging terminals with a lead for connection to a source of mains supply. Means may be provided to hold the apparatus in positive contact with the charging terminals.

Thus the lid of the apparatus could be lined with resilient material, e.g. foam rubber, and closing the lid could be arranged to hold the apparatus in positive contact. Alternatively the charging terminals could be spring loaded and the lid non resilient but such as to push the apparatus down against the terminals. In a further alternative a lip might be provided in the recess or at the edge thereof below which a portion of the apparatus could be pushed so as to clip it under the lip.

Many alternative ways of achieving this positive contact could be achieved and possibly even the weight of the apparatus itself might be sufficient e.g. if male terminals were provided in the case and female terminals in the end of the handle of the apparatus the apparatus could be pushed onto the terminals and held by the push fit, the male terminals being shrouded from accidental contact by the user by the walls of this hole shaped part of the recess which would accommodate the handle of the apparatus.

The charging circuit may be a built in transformer. The carrying case may have an adjustable mains input device e.g. adjustable between 220–240 volt A.C. input a 110–120 volt A.C. input or may be supplied in separate forms for the two voltages.

The mount of the carrying case may be provided with further recesses e.g. for sheaths and for the general view or wide angle unit.

In a modification the battery pack could be made demountable and a pair of battery packs could be provided and a second charging terminal provided for the battery pack which was not in use so that a pack could always be on charge and thus a highly charged pack would always be available for use. When the apparatus was not being used, e.g. overnight, both packs could be on charge.

In the preferred embodiment of the apparatus the batteries and lamp are sealed in and are designed to have an adequate battery life and lamp life.

The carrying case may also be provided with indicators associated with each charging terminal to indicate the state of charge of any battery attached to the terminal.

With the 4 watt lamp which is preferred the battery has a single charge life of 12 to 120 minutes e.g. 20–90 e.g. 40 minutes but for gynaecological inspections since each inspection will only take ½ to 3 minutes this will supply sufficient power for a day's work. The batteries can then be recharged slowly overnight to assist in maintaining a long battery life.

In order to assist with preserving battery life the switch for the light source is preferably arranged to return to the off position as soon as it is released, i.e. it has to be held "on".

Various references have been made to medical uses of the apparatus. These will now be described in more detail with particular reference to use of apparatus for vaginal inspection.

This aspect of the invention relates to apparatus for inspecting and obtaining smears and histological samples of the *cervix uteri* and vaginal mucosa of the human female without the necessity of dilating the vaginal walls or, in the case of *virgo intacta*, of interfering in any way with the structure of the hymenal membrane; and it is especially adapted to the vaginal and cervical examination of children who, while having passed the onset of menses, yet do not have fully grown or developed genitalia.

At the present time all means for such examinations depend upon the insertion into the vagina of an apparatus; e.g., a vaginal speculum, intended to dilate the vaginal walls so as to facilitate either direct inspection of the internal cavity by eye, or to facilitate the introduction of auxiliary instruments for indirect inspection and/or sample collection which are sufficiently large to prohibit their passage through the closed vagina or the orifice of the intact hymen without previous steps having been taken to increase the size of the natural opening.

In general, such techniques are distressing to the patient and are in many cases sufficiently painful to prohibit their use without anaesthetising the subject. It is common practice at present, except in such cases where illness is grave enough to warrant unusual procedures, to forego otherwise indicated examination of young subjects or virgins rather than cause such distress. Indeed, the requirement for dilation may cause some discomfort even to mature women who have given birth many times.

The general object of this aspect of the present invention is to facilitate such internal examination and collection of histological samples and in doing so the provisions afforded thereby reduce the necessary procedure to one which, with the facilities normally available to the general medical practitioner, would permit routine examination of patients where no examination can now conveniently be performed; would cause minimal distress, both mental and physical, to all patients and would provide equipment which is sufficiently compact, mobile and economical to form a part of the general practitioner's normal collection of instruments.

The invention in its preferred embodiments involves means which employ optical imaging and illumination techniques heretofore unutilised in gynaecological examination to transfer a magnified image of the cervical and vaginal tissues from a region proximal to said tissues to a screen or other display device remote from the tissue and outside the body cavity. By these means it obviates the need for dilation of the vaginal wall or distortion of the hymenal orifice.

The present invention is based on the discovery that a structure whose maximum diameter is less than that of the orifice present in the average intact hymen at onset of menses can be made to contain:

A. a rigid fiber bundle carrying illuminating light from a remote, relatively low powered extracorporeal light source to a region within the vaginal cavity proximal to the tissues under examination, B. a rigid aligned fiber bundle with imaging properties capable of collecting the illuminating light reflected from the tissues under examination and carrying this image out of the body cavity for magnification, display and inspection on a convenient remotely placed screen, C. devices for the collection of cervical and vaginal smears and/or histological samples which can be remotely operated and observed by means of the imaging fiber bundle during manipulation of the said collecting devices.

Moreover, this structure can be made sterile and thus suitable for use within a human body cavity.

Preferably the sheath is made of rigid transparent plastics material and is of substantially circular or elliptical or oval cross section and has a cross sectional area not more than 3.25 sq. cms. e.g. in the range 1.0 to 2.5 sq. cms. The thickness and surface configuration of the transparent distal end is desirably such as to minimize optical distortion, e.g. the thickness is of the order 0.012 inches or more broadly 0.005–0.020 inches.

A definition of a central plane for the device is that plane which contains the longitudinal axis of the said passageway for the sheath and also the longitudinal axis of the optical means in the said probe, i.e. the fiber optic bundle. Thus in one arrangement the longitudinal axis of the handle may pass through the centre of the image display means and through the longitudinal axis of the passageway for the sheath but still be at an angle to the central plane of the device as defined by reference to the axes of the passageway for the sheath and the fibre optic bundle in the probe.

Transverse planes of the device and vertical planes of the device may be defined as planes which pass through and are perpendicular to the said central plane anywhere between the distal end of the said sheath and the centre of the rearward base of the image display means and which are perpendicular to each other.

The handle preferably extends out such that its longitudinal axis is at an angle in the range of 10° to 70° e.g. to 50° or more preferably 45° to the said central transverse and vertical planes and preferably on the image display or rearward side of the housing with regard to the said probe. The handle may extend out in the transverse or vertical planes at right angles to the longitudinal axis.

Taking the center of the rearward face of the said image display means as the reference point, and taking a vertical plane of the device which contains the said centre as the reference plane, than the angle between the line in the said plane which joins the said centre and a point on the extended longitudinal axis of the handle and the other line in the said plane which joins the said centre at a point of the extended longitudinal axis of the passageway for the sheath may be 20° to 70° e.g. 45° but in order to achieve greater separation of the users hands and faciliate manipulation of a probe through the sheath the angle is preferably 110° to 210° e.g. 135° or more broadly the handle and the passageway are on opposite sides of the image display means.

The invention also extends to the disposable sheath itself.

Thus according to this aspect of the invention a disposable sheath, suitable for use with the apparatus of the invention, is made of rigid transparent plastic and which preferably has a substantially elliptical oval or circular cross section, and preferably has a cross section area in the range 0.2 to 3.25 sq. cms., has a first longitudinal duct preferably of circular cross section extending through the full length of the sheath, a second duct extending from a thin window at one end of the sheath, the distal end, to an opening adjacent the other end, the sheath preferably affording connecting means e.g. reducing in cross section at the said opening, the connecting means e.g., the portion of reduced cross section, being adapted to be releaseably secured to the housing of the apparatus e.g. releaseably secured in the said passageway of the housing of the apparatus.

The exterior of the sheath adjacent its distal end preferably affords a sample collecting portion, whereby withdrawal of the said duct defining means from the vaginal cavity causes a sample from the vaginal mucosa to be collected.

A convenient and efficient means of performing such examinations and/or operations is described below.

The invention may be put into practice in various ways and two specific embodiments and certain modifications will be described to illustrate the invention with reference to the accompanying drawings, in which:-

FIG. 11 shows the magazine in position in the handle of the device and is a view in the same direction as FIG. 2;

FIG. 12 shows the magazine alone and is a sectional view from the front and is in the opposite sense to FIG. 2;

FIG. 13 is a sectional view similar to FIG. 12;

Figure 1:
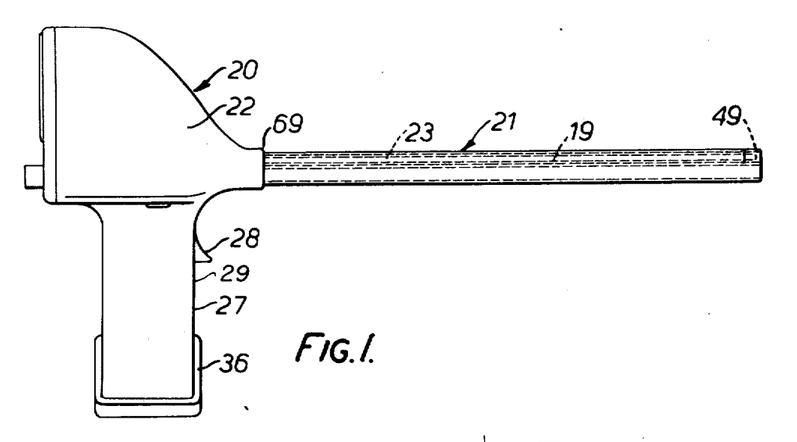
FIG. 1 is a side elevation of the inspection apparatus in accordance with the invention.
Figure 2:
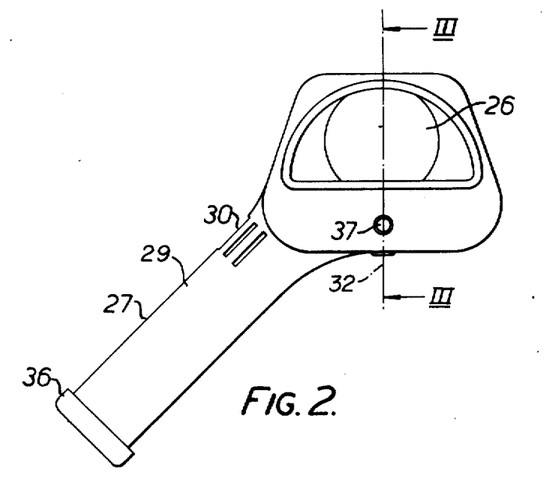
FIG. 2 is an end elevation of the apparatus shown in FIG. 1 showing the display panel.

The inspection apparatus consists of two main parts a reusable housing 20 carrying a probe 19 and a disposable sheath 21 both shown in FIG. 1.

Figure 3:
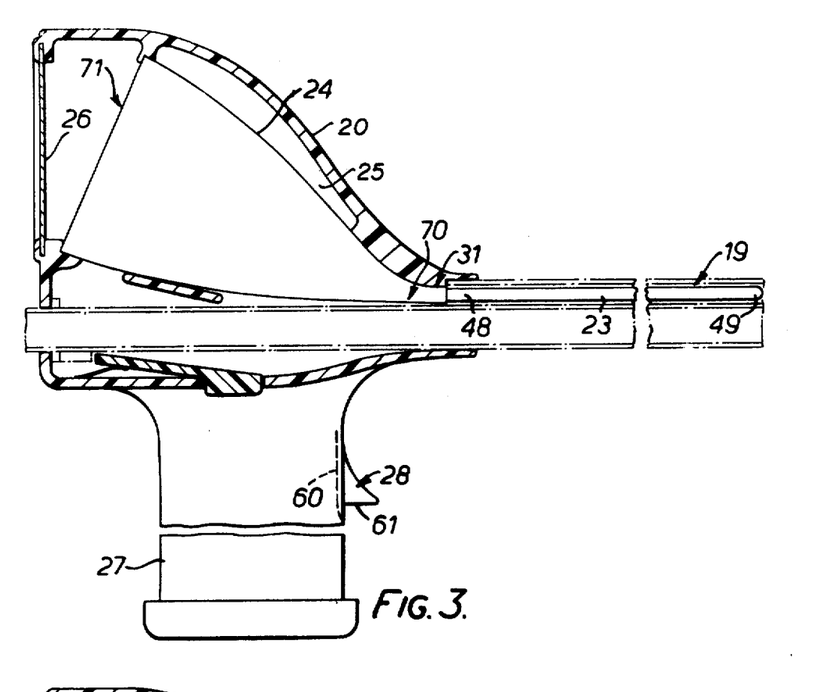
FIG. 3 is a cross section on the line III—III, (the centre plane of the device), of FIG. 2 showing the display portion of the apparatus shown in FIGS. 1 and 2, using a fused fibre optic cone to transmit the image to a display panel.
Figure 11:
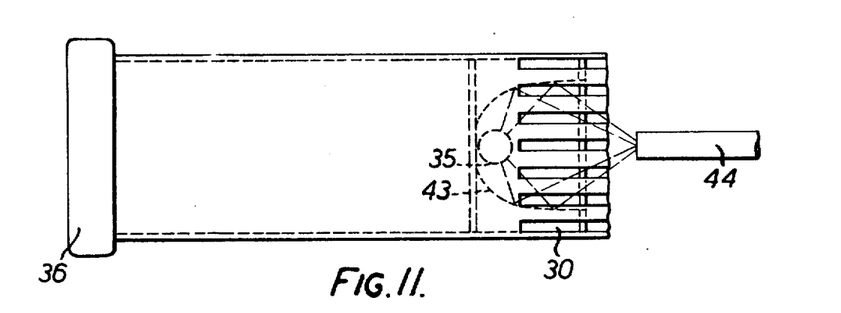
FIGS. 11 to 13 are part longitudinal sectional views of the handle and magazine of the device shown in FIG. 2 of an embodiment in which ellipsoidal reflector is used to focus light from a source located at one focus of the ellipse onto the end of an input fibre bundle which end is located at the other focus of the ellipse.
Figure 12:
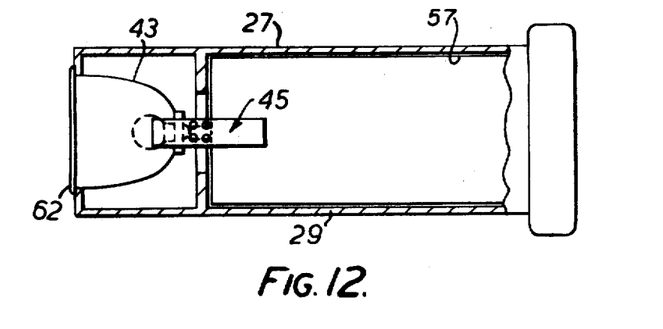
Figure 13:
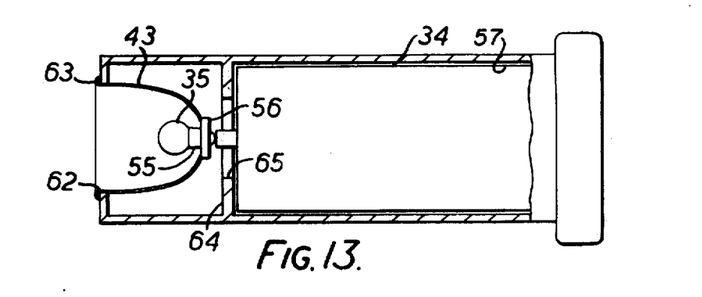

The reusable housing 20 and probe 19 are shown in more detail in FIGS. 1 and 3 (with a modification in FIG. 4) and in FIGS. 11 to 13. The disposable sheath 21 is shown in more detail in FIGS. 5 to 10. The device has a central plane 32.

Figure 4:
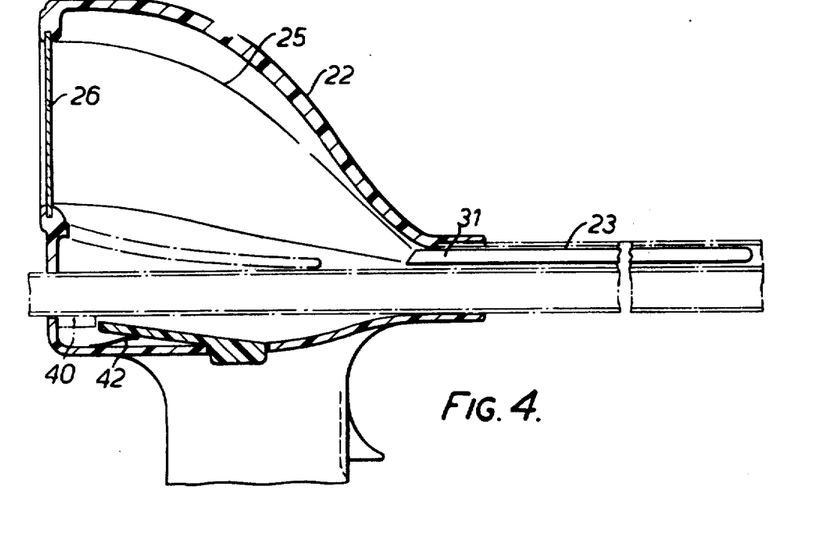
FIG. 4 is a view similar to FIG. 3 of a modification in which an optical lens train is used instead of a fused fibre optic cone.

The housing 20 comprises a body portion 22 enclosing and supporting an optical display system consisting of an image collecting fibre optic bundle 23 affording the probe 19 or part of it and a fused fibre optic cone 24 (in FIG. 3) or an optical train 25 leading light from the rear end 31 of the fibre bundle 23 to a ground glass display panel 26. The body portion has an integral handle 27 extending downwards and out to one side at 45° to the plane 32. An "on-off" trigger switch 28 extends through the front face of the handle 27 which has a roughened gripping surface 29. This switch is preferably arranged to return to the off position when released.

The housing, shown in FIGS. 1, 2, 3 and 4 is in this example moulded from a highly impact resistant high softening point, plastic such as polycarbonate. It is shaped as displayed in the drawings with suitable recesses and openings for buttons, switches, ancillary components and operating controls.

The handle encloses a power source 34 and light source 35 and convection ducts 30 are provided for cooling the light source. Instead of a power source or rechargeable source, a power cable could be used but this would make the device less readily handled. The end of the handle 27 is closed by a flange or end cap 36 which is part of the magazine which carries the power source and the light source.

A passageway 37 is formed through the bottom half of the housing on its central plane 32. This houses the disposable sheath 21 which is provided with a retaining ring 40 (see FIG. 5) by which it can be releaseably secured in the housing by means of a catch 41 biassed against a spring 42.

The handle 27 extends out at right angles to the longitudinal axis 33 of the passageway 37.

Figure 9:
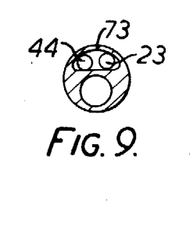
Figure 10:
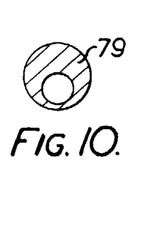

The handle 27 as mentioned above houses a light supply assembly. In one arrangement shown in FIGS. 11 to 13 the light source, a bulb, is positioned at one focus $F_1$ of an ellipsoidal reflector 43 and the end of a fiber optic bundle 44 is positioned at the other focus $F_2$ of the ellipsoidal reflector. The lamp 35 is supplied with power from the battery 34 under the control of the contact plate 45 forming part of the "on-off"pressure switch 28. The fiber optic bundle is then run up the handle through the housing and down parallel to the image collecting bundle 23 so as to terminate adjacent the end of the bundle 23 as shown in FIG. 9 these two bundles 23 and 44 can be located side by side. However other orientations are also possible.

In a preferred modification the fiber optic bundle 44 is used merely to transilluminate the portion 48 of the image collecting bundle 23 immediately in front of its rear end so that the bundle 23 in known manner carries out both the illuminating and image collecting function enabling the probe 19 to be made more compact. The sides of the sheath 21 when used can also be transilluminated and some further illumination of the region being observed can be achieved by this means.

Transillumination is a well known phenomena in fiber optic technology and detailed description is not thought necessary in view of the teaching that the image collecting bundle is to be used both for illumination and image collection. However the basic requirement is for the bundle 44 to illuminate at close range the side of the bundle 23 at an angle of about 45° with the light shining down the bundle 44 towards the front end 49 of the probe 19.

The magazine (see FIGS. 11 to 14) contains a light source 35 comprising a small doubly helically wound tungsten filament or quartz-halogen lamp not greater than 7.5 mm. in maximum dimension fixed in a holder 55 (see FIG. 13) which is in turn fixed by a threaded locking ring 56 in the usual manner to a suitably shaped silvered and polished reflector 43 in FIGS. 11 to 13. The magazine also contains a power supply consisting of a dry cell or cells 34 having a voltage of between 1.2 to 28 volts e.g. 6 to 24 e.g. 12 volts DC and whose overall dimensions are no greater than 65 × 30 × 30 mm. resting in a shaped compartment 57 in the magazine. The cell or cells 34 supplies current to the lamp 35. A similar wire is fixed from the lamp holder to the striker plate 60 of the same pressure switch 28. Fixed to the striker plate is a button 61 made of the same material as the casing 22 to which said striker plate is attached. The reflector 43 or 52 is a push-fit into a circular cut-out 62 in the magazine. A lip 63 around the edge of the reflector insures correct seating and alignment of the light source. A cut-out 65 in the central transverse wall 64 of the magazine facilitates replacement of the dry cell 34. The whole magazine is a push-fit into the handle portion 27 of the housing 20. The depth to which the magazine can penetrate the handle of the housing is established by the terminal flange or end cap 36 of the magazine.

The image collecting conduit 23, armoured and mounted, lies parallel to the illuminating fibre bundle in the horizontal plane of the housing. It is 2.5 mm. in diameter and is a rigid aligned bundle of $5\mu$ coated optical fibres. The image conduit is bent at point 70 and flares into the fibre cone 24 along the longitudinal axis of the cone. As the diameter of each fibre in the imaging bundle is $5\mu$ and the radius of curvature at point 70 is less than 1 mm., light loss over this region is negligible. As the diameter $a_1$ of the conduit 23 at point 70 is 2.5 mm. and the exit diameter of the cone 24

(point 71) is 40 mm., the photometric efficiency of the display system is seen to be $\phi = (a_1/a_2)^2 = 0.39$.

Two typical coated fibre materials, numerical apertures, N.A. = 0.56 and 0.099 may be taken as convenient examples of materials useful for the image collecting conduit 23. Taking the refractive index of the medium through which observation is made; i.e., the vaginal cavity, as effectively $n_3 = 1$, the acceptance angle of each fibre element is given by:

$$\theta = \arcsin \frac{(n_o^2 - n'^2)^{1/2}}{n_3}$$

$$= 34° \text{ for N.A.} = 0.56$$
$$= 5.75° \text{ for N.A.} = 0.099$$

At a maximal observational distance of 3 mm., this means that using proximal scanning, each fibre element of N.A. = 0.56 will observe an area 1.3 mm. in diameter.

For high resolution; i.e., the ability to distinguish very small features from relatively distant vantage points, the smaller numerical aperture, N.A. = 0.099, is superior. It would for example, provide resolution of elements 2 mm. in diameter from a viewing distance of 2 cm. In the first case, of course, considerably less illumination would be required and closer inspection of the tissues would be possible. In the second case a more general vantage could be used, but far more intense illumination would be required. Clearly, the fibre diameter, material and lamp are selected according to functional need.

The probe and housing are made of materials which could be autoclaved to render them sterile and thus the apparatus could be sterilized after each use by removing the magazine and immersing the remainder of the apparatus in the sterilizing medium.

Figures 14, 15:
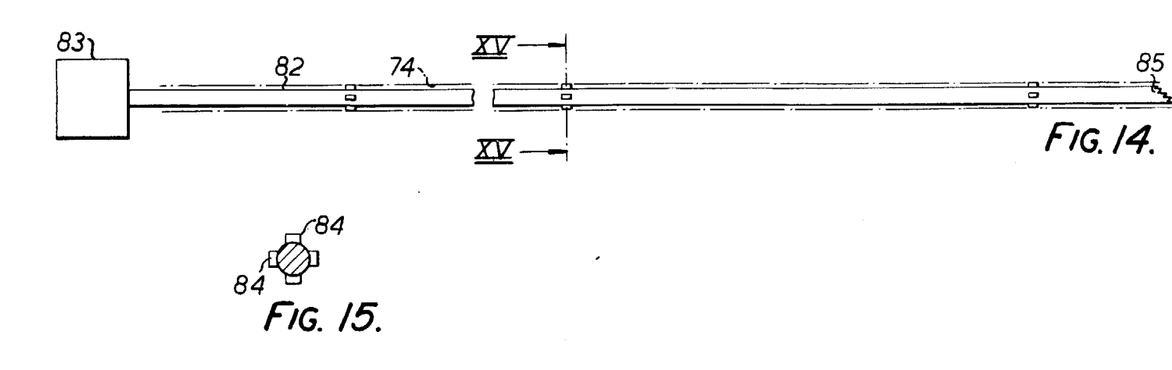
FIG. 14 is a longitudinal section similar to FIG. 5 of a fleche device suitable for use for collecting cervical smears or samples.
FIG. 15 is a cross sectional view of the rod portion of the fleche on the line XV—XV of FIG. 14, The first embodiment will now be described with reference to FIGS. 1 to 20.

In use the vaginal cavity would be observed through the probe with minimal dilation and the fleche shown in FIG. 14 introduced into and withdrawn from the vaginal cavity through the passageway 37 enabling samples to be collected whilst the sample area is observed.

However it is much to be preferred if autoclaving can be avoided and disposable units used instead. The disposable sheath 21 is thus provided in a preferred embodiment. This has the further advantage that the sample carrying end of the fleche can be withdrawn into the sheath after the sample has been collected and this prevents the end of the fleche contacting the vaginal walls during withdrawal and picking up additional cells other than those taken from the selected observed area of the cervix. The exterior of sheath can be used to collect samples from the vaginal walls as will be described below.

Figure 5:
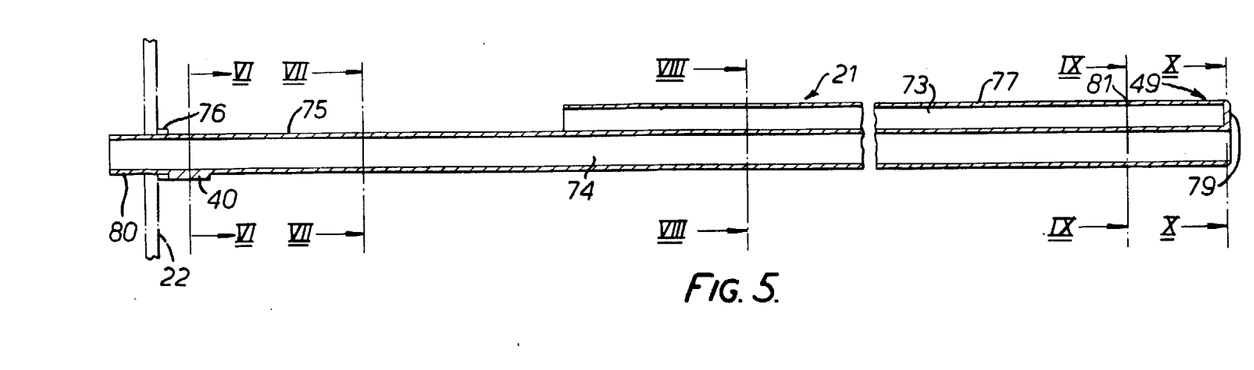
FIG. 5 is a longitudinal cross section on the line III—III of FIG. 2 showing the disposable sheath structure which enters the vaginal cavity.
Figure 6:
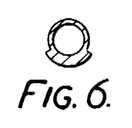
FIGS. 6 to 10 are cross sections on the lines VI—VI, VII—VII, VIII—VIII, IX—IX and X—X respectively of FIG. 5.
Figure 7:
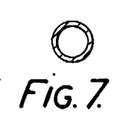
Figure 8:
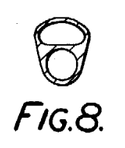

The sheath 21 is shown in longitudinal cross section in FIG. 5 and in transverse cross section in FIGS. 6 to 10. The sheath has an upper duct 73 for the optic fibre bundle or bundles 23 and 44 (see FIG. 9) and this duct can be of any suitable cross section. The sheath also has a lower duct 74 of circular cross section in which the fleche is located. The rear portion 75 of the sheath passes through the passageway 37 in the body portion 22 of the apparatus and carries a retaining ring 76 cut to allow entry past the cable. The retaining catch 40 is located just in front of the ring 76 and on the lower face of the sheath.

The front end 77 of the sheath is circular in cross section and about 1.0 to 2.0 cms. e.g. 1.4 cms. in diameter. The sheath closes off the end of the upper duct 73 forming a thin integral window 79 (see FIG. 10). The fibre optic cables 23 and 44 are thus completely enclosed by the sheath which can be made of PERSPEX or any other transparent inert disposable material. The distal ends of the fibre cables are in contact with the flat distal end 79 of the sheath. The lower portion of the sheath affords the hollow duct 74 which is of circular cross section along its full length. This facilitates the insertion and manipulation of the smear/sample collection device, the fleche, shown in FIG. 18 and further described below. The sheath in its entirety is detachable and is seated on the housing wall by the flange or retaining ring 76. It is retained in position by the catch 41 so that on release of the catch e.g. by pressure the used sheath can be allowed to fall out under its own weight. A portion 80 of the sheath projects beyond the rear of the housing 22 to facilitate insertion and removal of the fleche. The sheath itself acts as the collector of vaginal smears by means of a small step 81 formed around the outer surface of the sheath just to the rear of the plane of the section shown in FIG. 9.

The fleche, a device for collecting cervical smears and/or samples is a rod 82 of circular cross section with a cylindrical portion 83 (FIG. 14) at the proximal end the diameter of which is considerably greater than the diameter of the rod. By means of this knurled knob, the rod may be conveniently rotated in the sheath. The rod is maintained coaxial with the cylinder by means of three sets of four protuberances 84 or fins (see FIG. 15) spaced equally around the rod and bearing on the cylindrical wall of the duct 74. In this example the distal end 85 of the rod is shaped for the collection of a cervical smear.

In operation, the physician fits a sheath 21 into the housing 22 and inserts the sheath in to the vaginal cavity. Turning on the light source 25 by means of the switch 28, he illuminates the region to be examined, moving the entire apparatus as necessary to inspect the area. In order to collect a cervical smear a fleche is inserted into the rear end 80 of the duct 74 of the sheath, rested on the cervix and rotated by means of the knurled knob 83. The fleche is retracted slightly so that its distal end is located within the duct 74 and the whole apparatus removed from the body cavity. The sheath, which upon exit has collected a vaginal smear on the step 81, is then ejected by pressing the catch 41 with the apparatus probe downwards. The sheath with the probe contained within it can then be given a subsequent examination. It is desirably not re-used.

The optic fibre bundles can be of any desired cross section and need not be circular. Also when two optic fibre bundles are used the illuminating fibre bundle can be of lower quality than the image collecting bundle.

The sheath 21 can also be used to supply illumination (though it will be much less intense) by means of transillumination and internal reflection.

A fibre optic bundle has the advantage over a conventional lens system that it does not feed focusing due to the very high number of individual fibres.

Also even if a 7 or 8 mm. diameter lens system could be produced it would have to be housed in the duct 74 and this would mean that one would not be able to have simultaneous observation and smear collection.

The term fiber optic bundle means an array of fibers each of which acts as a waveguide. In order for such fibres to act as a waveguide the most usual structure of the fiber is to have a glass or transparent inner core having a relatively high index of refraction surrounded by a coating having a lower refractive index so as to cause internal reflection.

Fiber optic bundles can be made by the following general procedure.

A tube several inches e.g. 3 inches in diameter is formed from glass of lower refractive index e.g. 0.3. It is suspended vertically and a rod e.g. 2 inches in diameter of glass of higher refractive index e.g. 0.4 is placed inside it. The assembly is heated till molten and then drawn out into a very fine fiber. This is chopped up into short lengths e.g. 1 foot long and the fibers glued together e.g. with epoxy resin in a bundle e.g. 2 inches in diameter this is then suspended vertically and heated again until molten and then drawn out e.g. to 1 mm. diameter. The bundle can then be sheathed in metal or plastics for protection.

Thus according to a further aspect of the present invention apparatus adapted to the inspection of the interior of a cavity to which access can only be obtained via a restricted opening comprises first optical means suitable for feeding light into the cavity to illuminate at least a portion of the interior of the cavity and second optical means suitable for collecting an image of at least a portion of that part of the cavity which is illuminated and feeding the optical image to the outside of the cavity to image display means, the second optical means at least at its end juxtaposed to the display means being provided by an imaging fibre optic bundle, the display means being offset from the longitudinal axis of the second optical means and the said imaging fibre optic bundle being bent through an angle so that its output end is substantially parallel to and facing the display means and one or more lenses arranged to carry the image from the said end of the imaging fibre optic bundle to the display means, which may be a ground glass screen.

The said imaging fibre optic bundle is preferably a rigid fused fibre conduit which has been permanently bent to the desired curvature.

What I claim as my invention and desire to secure by Letters Patent is:

1. Apparatus adapted to be held in the hand for inspecting a cavity of restricted aperture comprising, a housing having a proximal and a distal end, a handle on said housing intermediate said proximal and distal ends, said housing formed with an aperture extending from said proximal end to said distal end, first optical means in said handle for generating light, second optical means in said housing for collecting a visible image, image display means in said proximal end of said housing to display an image received from said second optical means, said display means being visible from the proximal end of said housing, an elongated sheath removably inserted in said housing through said aperture with said sheath extending out the proximal end of said handle and beyond the distal end of said housing, latch means in said housing and said sheath for detachably securing said sheath in position extending through said housing, said sheath formed with a first and a second longitudinal duct, said first duct comprising an unobstructed passage from end to end of said sheath, and formed to detachably receive an elongated fleche, said fleche formed to sample matter from said cavity when said sheath is inserted into said cavity, said second duct terminating at the distal end of said sheath in a transparent window flush with the distal end of said sheath, first fibre optic means in said second duct extending from said first optical means to said window to conduct light to illuminate said cavity outside said window, and second fibre optic means in said second duct extending from said window to said second optical means.

2. Apparatus as claimed in claim 1 in which the image display means is a ground glass screen.

3. Apparatus as claimed in claim 1 in which the sheath is made of rigid transparent plastics material and has a cross sectional area not more than 3.25 sq. cms.

4. Apparatus as claimed in claim 1 in which the second optical means comprises a fibre optical cone.

5. Apparatus as claimed in claim 1 in which the second optical means for projecting the image onto the image display means comprises a lens system.

6. Apparatus as claimed in claim 1 in which said second fibre optic means comprises an imaging fibre optic bundle located within an annular fibre optic illuminating bundle which comprises the first fibre optic means, and the imaging fibre optic bundle has a numerical aperture in the range 0.2 to 0.8 to give a short depth of focus as low illumination.

7. Apparatus as claimed in claim 1 in which the first optical means are supplied with light from a self contained rechargeable battery and lamp pack incorporated in said handle.

8. Apparatus as claimed in claim 1 in which said first and second fibre optic means comprise at least one fibre optic bundle made up of a regular array of fibre optic elements and the first and second optical means are such that the light output from the end of the first fibre optic means is in the range 500 to 5000 foot Lamberts.

9. Apparatus as claimed in claim 1 in which the first optical means comprises a lamp of between 1 and 30 volts and 0.05 and 2.5 amps having a power range of from 0.1 to 30 watts.

10. Apparatus as claimed in claim 1 in which the first optical means comprises a light source having a lamp having a filament and an envelope of constant cross section located in said handle held in substantially fixed axial position by the housing and the proximal end of the first fibre optic means is located in a close fitting duct formed in the housing so that the end of the first fibre optic means is held close to the surface of the envelope of the lamp, thus closely aligning the filament of the lamp with the end of the fibre optic bundle.

11. Apparatus as claimed in claim 10 in which the spacing of the nearest part of the filament of the lamp from the end of said first fibre optic means is not greater than the diameter of said first fibre optic means.

12. Apparatus as claimed in claim 1 in which the handle is disposed asymmetrically with regard to the aperature.

* * * * *